(12) United States Patent
Boche et al.

(10) Patent No.: US 6,635,071 B2
(45) Date of Patent: Oct. 21, 2003

(54) SURGICAL GRASPING AND HOLDING FORCEPS

(75) Inventors: Hartmut Boche, Immenstaad (DE); Hans Scherieble, Esslingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/938,702

(22) Filed: Aug. 24, 2001

(65) Prior Publication Data

US 2002/0002385 A1 Jan. 3, 2002

Related U.S. Application Data

(62) Division of application No. 09/274,419, filed on Mar. 22, 1999, now Pat. No. 6,280,458, which is a continuation of application No. PCT/EP98/04576, filed on Jul. 21, 1998.

(30) Foreign Application Priority Data

Jul. 22, 1997 (DE) .......................... 197 31 454

(51) Int. Cl.⁷ .............................................. A61B 17/28
(52) U.S. Cl. ...................................................... 606/206
(58) Field of Search ................................ 606/206, 208, 606/205, 210; 600/564; 81/318; 294/116, 106

(56) References Cited

U.S. PATENT DOCUMENTS

| | | | | |
|---|---|---|---|---|
| 2,114,695 A | * | 4/1938 | Anderson | |
| 4,174,715 A | | 11/1979 | Hasson | 128/321 |
| 5,211,655 A | | 5/1993 | Hasson | 606/205 |
| 5,308,357 A | * | 5/1994 | Lichtman | |
| 5,354,313 A | | 10/1994 | Boebel | 606/208 |
| 5,383,895 A | | 1/1995 | Holmes et al. | 606/206 |
| 5,409,478 A | | 4/1995 | Gerry et al. | 606/1 |
| 5,431,675 A | | 7/1995 | Nicholas et al. | 606/170 |
| 5,498,256 A | | 3/1996 | Furnish | 606/1 |

FOREIGN PATENT DOCUMENTS

| | | |
|---|---|---|
| DE | 9109097 | 10/1991 |
| DE | 4216971 A1 | 11/1993 |
| DE | 19731454 A1 | 3/1999 |
| EP | 0512725 A1 | 4/1992 |
| EP | 0688534 A1 | 5/1995 |

OTHER PUBLICATIONS

Storz Die Welt Der Endoskope; Praperier–Und Fasszangen; Take–Apart–Drehbar; Auszug Aus Katalog Endoskopische Chirurgie; 2.Ausgabe 1/94.

* cited by examiner

Primary Examiner—Michael H. Thaler
(74) Attorney, Agent, or Firm—St.Onge Steward Johnson & Reens, LLC

(57) ABSTRACT

A surgical grasping and holding forceps has a shaft, at least two mouth parts and a grip. A mechanism for opening and closing the mouth parts is in working engagement with the grip. The mechanism is acted upon by spring force in such a way that the mouth parts are pushed in a closing direction. A device, configured as a rigid linkage and engaging into said mechanism with which device said mouth parts are positively movable into a defined final closed position in which they exert a predefined holding force on an object received between them is provided. Said device has a stop which prevents overshooting of said final closed position, even when greater force is applied.

7 Claims, 5 Drawing Sheets

SURGICAL GRASPING AND HOLDING FORCEPS

PRIOR APPLICATIONS

This application is a Divisional of application Ser. No. 09/274,419 filed on Mar. 22, 1999 now U.S. Pat. No. 6,280,458 which is a continuation of and claims priority from International Application No. PCT/EP98/04576 filed Jul. 21, 1998, which claims priority from Germany Application No. 197 31 454.6 filed Jul. 22, 1997.

BACKGROUND OF THE INVENTION

The present invention relates to a surgical grasping and holding forceps.

Surgical grasping and holding forceps are used to grasp and hold and object between the mouth parts. Objects of this kind are, for example, spherical muslin sponges, in which case the term "sponge forceps" is used. In many laparoscopic operations, dissection sponges or rod sponges are required; these are used to remove tissue fluids or blood. One principal area of application is the actual dissection technique using the spherical sponge clamped and held between mouth parts. Sliding dissection is used to separate tissue layers atraumatically, and this reveal underlying structures during an operation. In these cases the sponge forceps operates simultaneously as a dissection forceps. Other objects that can be clamped in grasping and holding forceps of this kind are, for example, needles for making a suture.

The objects, i.e. for example a spherical sponge or a needle, are clamped into the holding forceps by the instrument nurse, and handed to the surgeon. The latter guides the holding forceps, for example with the sponge, through a trocar and dissects. After use, the holding forceps is withdrawn from the trocar and, if necessary, spherical muslin sponges are once again clamped in place. The same applies to the making of surgical sutures.

RELATED PRIOR ART

Grasping, holding, and dissection forceps are known from the catalog "Endoskopische Chirurgie [Endoscopic surgery], 2nd edition, 1/94, section 4, page DG 5, 'Präparier- und Faβzangen' [Dissection and grasping forceps]" of Karl Storz GmbH & Co., Tuttlingen, Germany.

Locking of the handle elements in a specific pivoted position relative to one another, and thus also locking of the mouth parts in a specific closed position, is brought about via a snap catch. The catch is configured as a notched bar that is arranged on one of the two handle elements. Corresponding projections which can snap into the notches are present on the other handle element. A spring or a lever holds the handle elements in the snapped-in or locked state. A plurality of locked positions are possible.

It has now been found, in practical utilization of this kind of surgical grasping and holding forceps, that during handling an attempt is made to clamp the object being held, for example a spherical sponge, as firmly as possible in the grasping forceps. The movable handle element is configured as a lever, the lever axis being represented by the hinge axis at which that movable handle element is articulated on the other handle element. The distance between the hinge axis and the point at which the movable handle element is joined to the actuation element that is to be displaced is substantially shorter than the distance from the hinge axis to the finger loop, arranged at the outer end of the handle element, into which is inserted the finger of a hand which grips the surgical grasping and holding forceps. The ratio is approximately 10:1, i.e. the closing force of a hand (approximately 10 kp) is magnified tenfold by the lever effect, i.e. to approximately 100 kp.

Because of the aforementioned practice of clamping a spherical sponge as firmly as possible in the grasping forceps, the lever mechanism means that the mouth parts are acted upon by large forces which can result in the mouth parts being bent and/or in damage to the mechanism, so that the sponge is no longer held firmly and can be lost during dissection. In such a case the lost sponge must be looked for within the body and picked up again. The lock in the form of the toothed-rack catch is also exposed to the high stress of this holding pressure, creating the risk that clumsy handling might cause the snap catch to unsnap, thus releasing the lock and opening the mouth parts.

It was also found in practical use that the handle elements protruding approximately at right angles from the shaft at the proximal end of the shaft greatly restrict the surgeon's mobility, so that for dissection purposes the forceps is gripped in the region of the transition from the shaft to the stationary handle part. The laterally protruding handle parts impede or interfere with the surgeon during dissection. In dissection operations of this kind, the snap catch which extends transversely between the two handle elements can inadvertently release, so that the objects held by the mouth parts, for example a spherical sponge or a needle, can be lost in the body.

DE-A-4 216 971 recites a forceps having two mouth parts for grasping and holding tissue or the like. At least one mouth part is pivotable relative to the other by axial adjustment of an actuation bar using a handle. The closed position of the mouth parts and the handle can be fixed in position by a lock, and the closing force of the forceps mouth parts can be set to different values.

EP-A-0 688 534 describes a hollow-shaft surgical instrument having a shaft and a push/pull rod displaceably mounted therein for moving a tool at the end of the shaft, and a handle element arranged coaxially with the shaft at the other end of the shaft in which a handle is mounted pivotably about a rotation axis running perpendicular to the longitudinal shaft axis, movement of the handle being transferable via linkage means to the push/pull rod. Also provided is a resilient snap element which, upon movement of the handle out of an initial position, is moved past a snap catch, thereby engages thereinto, and as a result prevents the handle from moving backward. To simplify the design, the snap element and the snap catch form a recirculating catch in which the snap element is moved, at the end of the handle's linear stroke, completely past the snap catch, and during the return movement moves past the back side of the snap catch into the initial position.

EP-A-0 512 725 discloses a medical instrument in which a mechanism for opening and closing the mouth parts is acted upon by spring force in such a way that the mouth parts are thereby pressed in the closing direction. Opening of the mouth parts can be controlled by way of an actuation element that is displaced against the force of the spring. When the actuation element is released, it is displaced by the spring and the mouth parts are thereby pressed toward one another in accordance with the force of the spring.

U.S. Pat. No. 5,431,675 discloses an interlock mechanism for a medical instrument in which a lever linkage is connected to a rotatable control cam. As a result of an eccentric arrangement of the lever on the cam and a corresponding configuration of the lever linkage, mouth parts can be moved positively into a very specific final closed position, and there hold the part present between the mouth parts with a specific holding force.

U.S. Pat. No. 5,409,478 recites a grip of a medical instrument on which a laterally protruding lever is articulated. This lever is connected via a further lever to an actuation element for moving the mouth parts. The actuation element itself is pressed by the force of a spring in one direction. The laterally protruding articulated lever can be laid by manual force against the grip, in the course of which the actuation element is displaced via the second lever against the force of the spring. The result is to overcome a spring catch, ensuring that when the articulated lever is released, it does not spread apart again.

U.S. Pat. No. 5,383,895 discloses a surgical instrument, configured as a grasping forceps, whose actuation element, which is provided for spreading and closing the mouth parts, can be moved back and forth against the force of a spring. The spring force acts on the actuation element in such a way as to press the mouth parts in the closing direction.

U.S. Pat. No. 5,211,655 discloses a medical forceps which is equipped with a lock with which the mouth parts can be locked in a very specific position.

It is the object of the present invention to create a surgical grasping and holding forceps which allows secure handling, and which in particular eliminates the possibility of damage to the part being grasped due to excessive application of a holding force.

SUMMARY OF THE INVENTION

According to the present invention, the object is achieved by a surgical grasping and holding forceps having a shaft with at least two mouth parts which are arranged at the distal end of the shaft; having a grip which is arranged at the proximal end of the shaft; having a mechanism, in working engagement with the grip, for opening and closing the mouth parts, the mechanism being acted upon by spring force in such a way that the mouth parts are thereby pushed in the closing direction, and the mechanism being movable against the spring force, by manipulation at the grip, in such a way that the mouth parts open; and having a lock for locking the mouth parts in a specific position, there being provided an device, configured as a rigid linkage and engaging into the mechanism, with which the mouth parts are positively movable into a defined final closed position in which they exert a predefined holding force on an object received between them, the device having a stop which prevents overshooting of the final closed position even when greater force is applied, and the lock locking the mouth parts in that final closed position.

The provision of an device configured as a rigid linkage, by means of which the mouth parts are positively movable into a defined final closed position, means that uncontrolled movements going beyond a final closed position are prevented. This prevents damage due to excessive pressure on the mouth parts. It is thereby also possible to prevent, for example, a muslin sponge from being damaged or even cut into several pieces by excessive clamping between the mouth parts. This is additionally assisted, advantageously, by the fact that the device is configured so that in the final closed position, a predetermined holding force is exerted on the objects received between the mouth parts. If a spherical muslin sponge is being gripped with a forceps according to the present invention, it is held with a very specific holding force which on the one hand is sufficient so that the sponge is not lost in the body during dissection operations, but on the other hand ensures that the sponge is not damaged by excessive holding forces, thus preventing the muslin sponge from being split into several parts or lost during dissection.

The fact that the device has a stop which prevents overshooting of the final closed position even when greater force is applied ensures that the mouth parts cannot be moved beyond the final closed position even when squeezed particularly strongly. These excessive forces are then absorbed by the stop of the device, which can be of correspondingly stable or solid configuration, and do not need to be absorbed by the sensitive components of the mechanism for controlling the mouth parts, said components being correspondingly thin in the case of very slender devices. The device thus acts as a "static force limiter."

The fact that the lock is configured so that the mouth parts are locked precisely in the final closed position simplifies handling and enhances reliability. In the case of the forceps mentioned initially with the toothed-rack snap catch, numerous locking possibilities existed. What now exists is one specific locking possibility, specifically at the point where the mouth parts have reached the final end position. It is therefore no longer necessary for the operator to decide about the mouth part closing position in which the lock is to be locked; instead, this takes place in defined fashion in the final closed position. Since mechanical locks are usually associated with a typical "locking click," the operator knows that the final position has been reached so that no further force needs to be exerted on the grip. The control mechanism of the device for moving the mouth parts into the defined final end position can be of various configurations. It is connected to the mouth parts and moves them in defined fashion into the final closed position.

The device is connected to the correspondingly designed mechanism in order, in the first portion of the closing angle range, to receive the object and hold it before the predefined holding force is applied. The principle of action of the present invention thus results from the succession of the two following action ranges:

Action Range of the Mechanism

Receiving and holding the object by spring force, i.e. applying a "pre-holding" force and axially moving the mechanism until the action range of the device is entered.

Action Range of the Device

Applying a predetermined holding force, and locking.

The delimitation of force in the handling of surgical grasping and holding forceps yields reproducible holding forces at the mouth parts, with advantageous consequences in terms of product liability.

In a particularly preferred embodiment of the invention, the grip is configured as a grip extending longitudinally in the shaft axis, and the mechanism and the device are received in the grip.

The considerable advantage of this feature is that a particularly ergonomic grip configuration is created by the fact that the entire grip extends along the shaft axis. In this configuration, there are no longer any laterally protruding scissor-like grip elements which impede the operator during handling, for example during a dissection operation. The forceps can thus be grasped at the ergonomic, roughly rod-shaped grip, and the surgical grasping and holding forceps can thus be gripped and manipulated in easily and reliably handled fashion.

In a further embodiment of the invention, a section of the grip is rotatable about the shaft axis, that section being part of the device, and the device being configured such that the mouth parts are movable into the final closed position by way of the rotary movement of the grip.

The advantage of this feature is that the device, and the closing movement of the mouth parts generated by it, are no longer implemented by pivoting of a scissor-like movable handle element, but rather by a simple rotary movement of the movable grip section.

In a further embodiment of the invention, there is configured in the grip a gated guide by way of which the rotary movement of the rotatable section of the grip can be converted into an axial displacement movement of an actuation element of the mechanism, the actuation element being connected to the mouth parts.

The advantage of this feature is that the rotary movement of the rotatable section of the grip is converted into the axial displacement movement of the actuation element for closing the mouth parts by way of mechanically simple and robust means.

In a further embodiment of the invention, the actuation element is displaceable in one direction along the shaft axis against the force of a spring, and displacement in that direction allows the mouth parts to open to their maximum opening position.

This feature has the considerable advantage, in terms of handling, that opening of the mouth parts, for example to introduce a muslin sponge between them, requires nothing more than a slight axial displacement of the actuation element in the shaft against the force of the spring. This can easily be done due to the fact that the actuation element projects proximally some-what beyond the grip; the latter is pressed on in this projecting region with the thumb and the actuation element is thereby displaced against the force of the spring. Once the object, for example a muslin sponge, has been brought between the maximally opened mouth parts, the actuation element is released and the spring displaces the actuation element in the opposite direction, so that the mouth parts are moved in the closing direction and already exert, on the object grasped between them, a certain holding force which is at least sufficient for the object not to fall out of the forceps. The device by which the mouth parts are moved in defined fashion into the final closed position is then actuated. This division into two partial steps is particularly convenient in terms of handling, and allows, in the first step when the mouth parts are maximally opened, exact positioning of the object, for example a muslin sponge, between the mouth parts; then in the second step the defined holding force is exerted via the device in the final closed position.

In a further embodiment of the invention, the actuation element is joined to a gate body which engages into a gate that belongs to the rotatable section of the grip.

The advantage of this feature is that with simple design means and a small number of components, a nonpositive connection is created between the components and converts the rotary movement of the grip into the corresponding linear movement of the actuation and then into the closing movement of the mouth parts. Components with this kind of simple mechanical design are also easy to clean and sterilize, thus further enhancing handling convenience and reliability.

In a further embodiment of the invention, the gate is configured as a hollow-cylindrical rotatable section of the grip which surrounds the gate body.

The advantage of this feature is that the hollow-cylindrical geometry yields a structure which can readily absorb even excessive applications of rotational forces, even if the construction of the forceps is very slender.

In a further embodiment of the invention, the gate body has two diametrically opposite, radially projecting pins which engage into a circumferential groove, rising in the axial direction, of the gate.

This symmetrical arrangement of the double gate guide constitutes a particular good and reliable gated guide which is also capable of uniformly distributing excessive forces exerted on the gate while preventing the occurrence of deformations.

In a further embodiment of the invention, each rising groove has an axially extending section.

The advantage of this feature is that the gate body, together with the actuation element, can be displaced axially over the axially extending section of the gate body so that in the first movement range, the mouth parts can be maximally spread to allow the object to be placed between them. After the actuation element has been released, the mouth parts move, because of the force of the spring, into a closed position with a "preholding" force. This axially extending section is then adjoined by the section of the groove which rises in the axial direction, by way of which the movement of the device which pivots the mouth parts into the final closed position is controlled.

In a further embodiment of the invention, each groove has an end section which slopes downward slightly in the axial direction with respect to the rising section.

The advantage of this feature is that the pins which are guided by the groove are moved, once a maximum axial movement distance has been exceeded, into a kind of undercut of the downward-sloping section. In order to open the mouth parts, the pins must first be moved, against the force of the gate which acts, proceeding from the resistance of the object held by the mouth parts, via the mouth parts and the actuation element on the gate, out of the lowest point of the downward-sloping section past the cam maximum; this requires exertion of a certain force. This prevents the inherent geometry of the rising groove from exerting a return torque such that the mouth parts open by themselves. The downward-sloping section of the groove thus already represents a lock for the mouth parts in the final closed position.

In a further embodiment of the invention, a closed end of the end section of the groove forms the stop.

The advantage of this feature is that means of particularly simple design are used to form the stop which prevents further rotation, i.e. overrotation. Excessive forces can be dissipated or distributed from the closed end of the groove via the gate, without acting on the mouth parts.

In a further embodiment of the invention, the lock acts between a stationary grip section and the rotatable section in such a way that the lock automatically closes when the pins of the gate body have reached the stop.

This feature has the considerable advantage, in terms of handling, that the lock closes precisely when the pins have reached the stop, and the mouth parts are therefore then locked precisely in the desired position, i.e. in the final closed position.

This is particularly convenient in terms of handling because the movable grip element merely needs to be rotated until the operator feels a resistance, specifically when the pins of the gate body have reached the end of the groove; and the lock closes automatically precisely in that position; this can be detected, for example, by way of the typical "locking click," thereby allowing the operator to recognize that the final closed position has been reached.

In a further embodiment of the invention, the lock has a spring-loaded axially extending stud which, when the rotatable grip section is in its final closed position, can be moved in axially inhibiting fashion and inhibits any relative rotation between the stationary grip section and rotatable grip section.

The design advantage of this feature is that it can implemented with mechanically simple means; the stud can also help distribute and dissipate excessive rotational forces over the entire grip.

In a further embodiment of the invention, the stud is joined to a slide element that is movable from the outside but is adapted to the outer contour of the grip.

The advantage of this feature is on the one hand that the lock can easily be released because of the accessibility from outside. The fact that the lock is adapted to the outer contour of the grip prevents said lock from being inadvertently released during manipulation, thus greatly enhancing reliability.

In a further embodiment of the invention, the grip has a cylindrical section, joined immovably to the shaft and coaxial with it, onto which the hollow-cylindrical rotatable element is slid, the rotatable element and the stationary section being secured against axial removal via a releasable interlock.

The advantage of this feature is that the grip can be assembled and also disassembled, for example for purposes of cleaning and sterilization, using features of simple design.

In a further embodiment of the invention, a closure cap is immovably mounted on the rotatable element.

The advantage of this feature is that the rotatable element, which operates as the gate and is cut through in the groove region, is closed off on the outside by the closure cap so that no contamination can penetrate. The closure cap can then have a corresponding ergonomic outer contour, for example grip recesses or the like, with which the rotary movement can be performed in ergonomic and conveniently handled fashion.

In a further embodiment of the invention, two grasping mouth parts are provided, the cross-sectional profile of each one being approximately semi-oval in shape and the closed mouth parts forming approximately an oval.

The advantage of this feature is not only that a favorable geometry is present with very slender components, so that the closing forces can be exerted without deformation, but also that when the mouth parts are closed the resulting geometry allows outstanding dissection, so that the forceps can be used as a dissection forceps.

In a further embodiment of the invention, one mouth part has an axially extending V-groove and the other mouth part has a tooth which can engage into the V-groove.

The advantage of this feature is that radial and axial forces which act on the object held by the mouth parts, for example a muslin sponge, during dissection are absorbed by the mouth parts via the tooth engagement, to prevent loss of the object during use. Lateral loads are absorbed by the V-shaped groove in the axial direction, while the tooth in the other mouth part, which engages into the V-groove, absorbs axial loads.

In an alternative embodiment, the device has at least one lever, articulated on the grip, whose one end is in engagement with the mechanism for opening and closing the mouth parts, and whose other end is swung out laterally when the mouth parts are in the open position, the other end being swingable onto the grip in order to move the mouth parts into the final closed position D.

In this alternative, the defined movement into the final closed position is performed by way of at least one lever; this has the advantage, in contrast to the solution using the rotatable grip element, that by configuring the lever geometry appropriately, the necessary holding force can easily be applied by the operator.

In a further embodiment of the invention, in the final closed position D the at least one lever extends along the elongated grip.

The advantage of this feature is that in the final closed position the lever does not protrude in obstructive fashion and thus does not interfere with the operator's freedom of movement and handling.

In a further embodiment of the invention, there is cut out from the grip a longitudinal groove into which the at least one lever can be snugly received when the mouth parts are in the final closed position so that it does not project beyond the contour of the grip.

In this embodiment, the retracted lever conforms fully to the outer contour of the grip, so that the lever does not in any way impair handling when the mouth parts are in the final closed position.

In a further embodiment of the invention, two levers, arranged diametrically opposite one another, are provided.

The advantage of this feature is that the forces for moving the mouth parts into the final closed position act symmetrically through the two levers on the mechanism for opening and closing, thereby eliminating the risk of bending the forceps due to unilaterally acting forces.

In a further embodiment of the invention, the lock is configured as a slide bushing which, when the lever is swung onto the grip, can be slid over it and keeps it from swinging outward.

The advantage of this feature is that the lock in the final closed position is implemented using easily handled components of simple design.

In a further embodiment of the invention, the slide bushing is locked in the final closed position by way of a ball catch.

The advantage of this feature is that the slide bushing which keeps the level from swinging outward is further locked by the ball catch in a very specific position.

In a further embodiment of the invention, the mechanism for opening and closing the mouth parts has an actuation element, axially displaceable on the shaft, which is connected to the one end of the lever in such a way that the pivoting movement of the lever can be converted into an axial displacement movement of the actuation element.

With this embodiment of the lever as a toggle lever, the pivot movements of the lever can be converted, with mechanically simple and robust means, into the axial displacement movement of the actuation element in the shaft.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be explained and described in further detail below with reference to a selected exemplifying embodiment, in conjunction with the attached drawings in which.

DETAILED DESCRIPTION OF PREFERRED EMBODIMENTS

Figure 1:
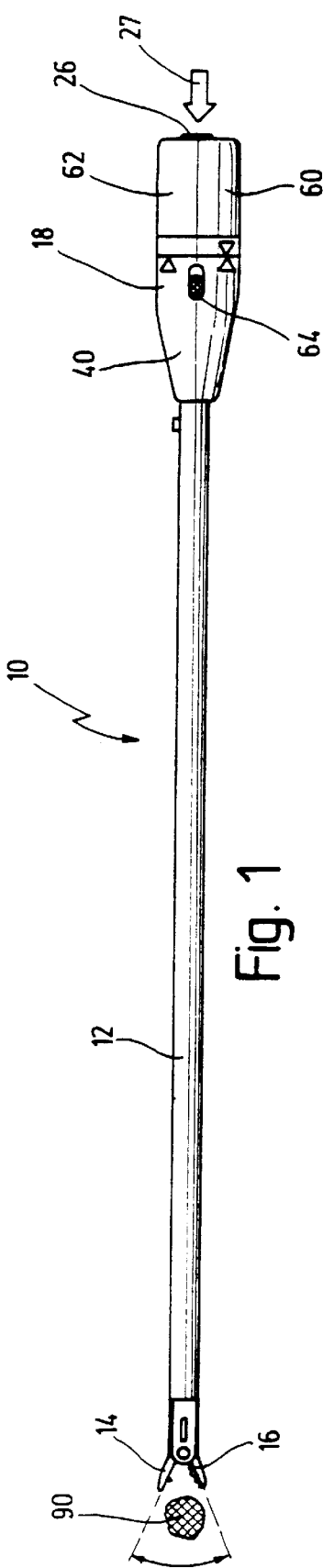
FIG. 1 shows a side view of a first embodiment of a surgical grasping and holding forceps with maximally opened mouth parts, i.e. the device is in the "open" position.
Figure 2:
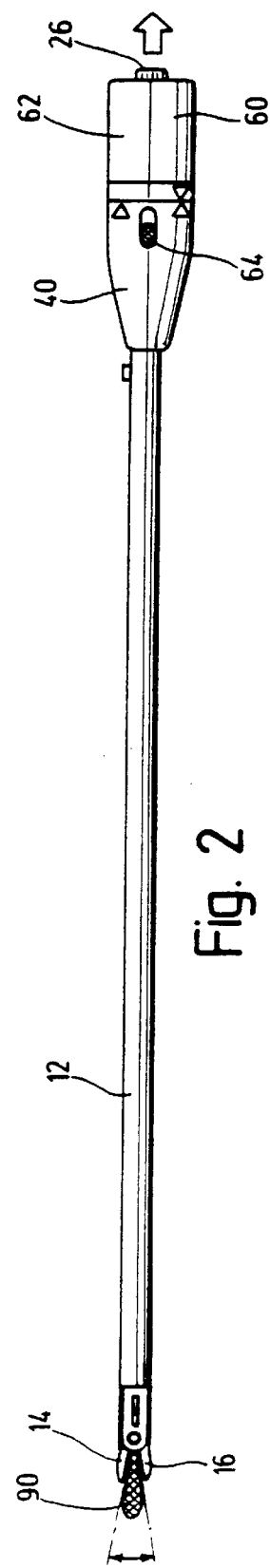
FIG. 2 shows a side view, corresponding to FIG. 1, in an intermediate position in which the mouth parts are already holding an object, in this case a spherical muslin sponge, with a certain pre-holding force.
Figure 3:
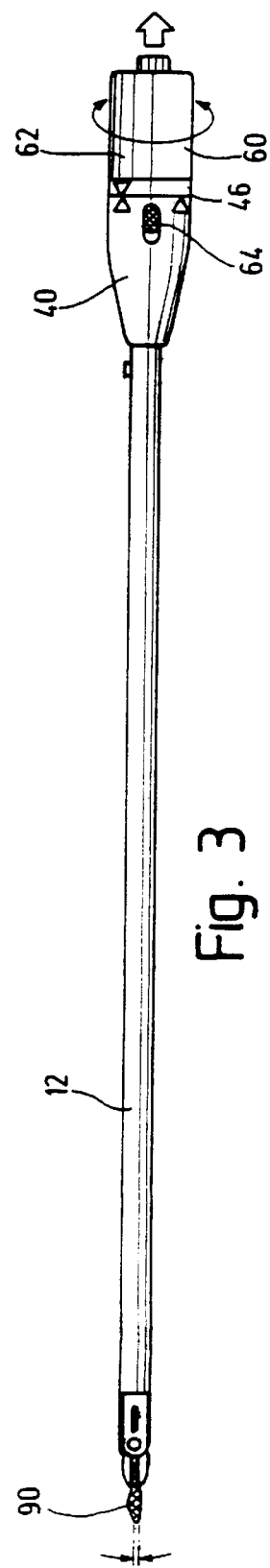
FIG. 3 shows a side view, corresponding to FIGS. 1 and 2, in which the mouth parts have been moved into the final closed position.

A surgical grasping and holding forceps, shown in FIGS. 1 through 3, is labeled in its entirety with the reference number 10.

Forceps 10 has an elongated cylindrical shaft 12 at whose distal end two mouth parts 14 and 16 are arranged. Arranged at the proximal end of shaft 12 is an approximately rod-shaped grip 18 extending longitudinally in the shaft axis.

Figure 4:
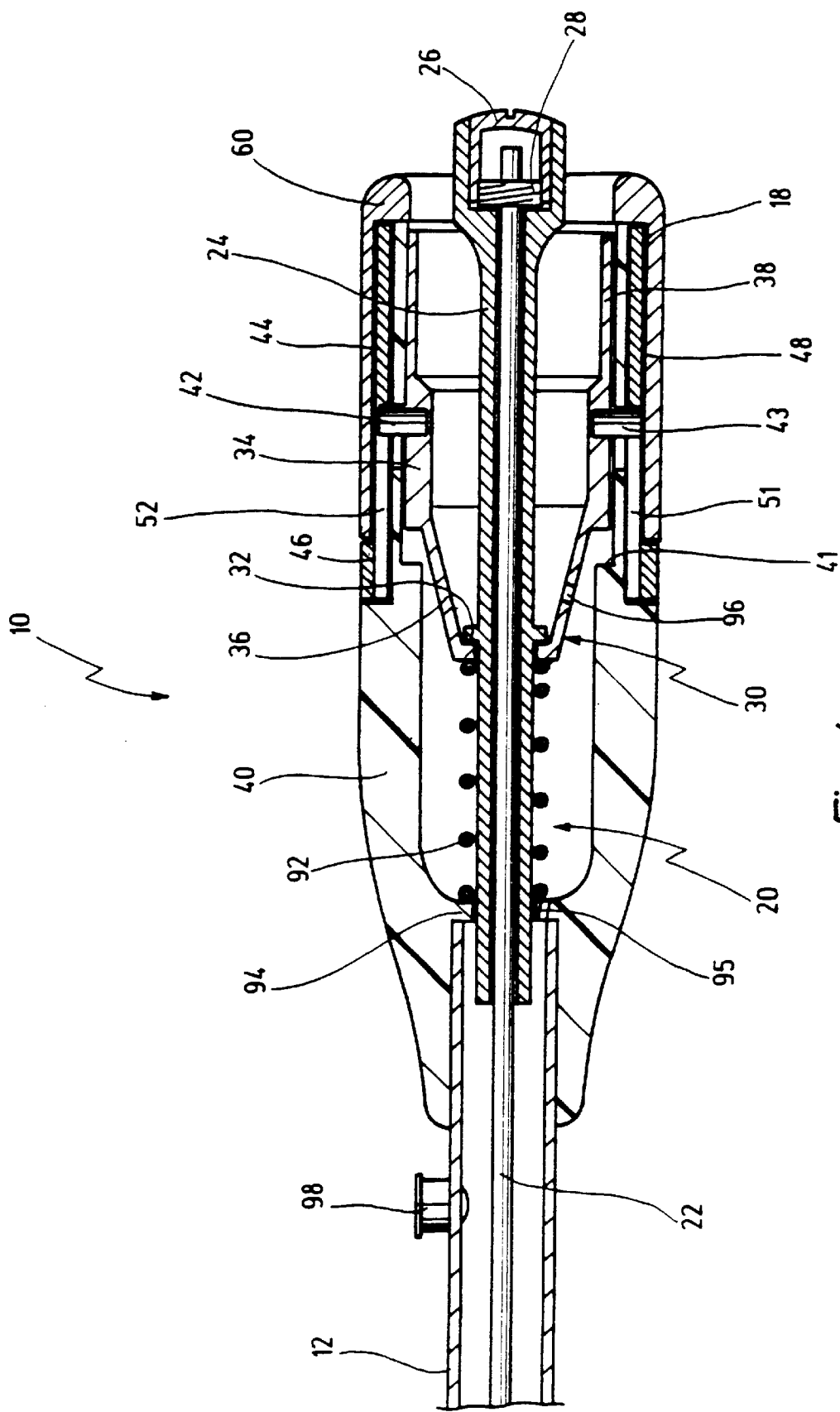
FIG. 4 shows a longitudinal section of a grip of the device of FIG. 3, in a position in which the mouth parts are closed.

A mechanism 20 for moving mouth parts 14 and 16 is received in grip 18, as is evident in particular from the section view of FIG. 4.

Mechanism 20 has a rod-shaped actuation element 22 which passes through shaft 12 and is connected at the distal end via a toggle lever linkage (not shown here) to the two mouth parts 14 and 16, as is known per se for forceps of this kind. At the proximal end, actuation element 22 extends out slightly beyond the end of grip 18, and a pusher sleeve 24 is slid over the end region of actuation element 22.

Pusher sleeve 24 has an end-mounted pusher 26, and pusher sleeve 24 extends beyond an inner flange 94 in grip 18 in the direction of shaft 12.

An adjusting screw 28, which is threaded onto threads of actuation element 22, is arranged in pusher 26. The relative displacement position between pusher sleeve 24 and actuation element 22 can be adjusted within a certain range, and made evident, by way of adjusting screw 28.

A gate body 34 is slid onto a actuation element 22 from its distal end until said body has arrived at an annular flange 32 of the pusher sleeve 24.

Gate body 34 has a conical section 36 which continues proximally into a cylindrical section 38. The outside diameter of cylindrical section 38 of gate body 34 is such that it corresponds approximately to the inside diameter of a cylindrical end section of a housing 40 that is immovably joined to shaft 12.

The distance between the distal end of cylindrical section 38 and a step 41 on the interior of housing 40 is such that the mouth parts can be opened by pressure on pusher 26 and corresponding displacement of actuation element 22.

Two radially projecting pins 42 and 43 protrude in diametrically opposite fashion from cylindrical section 38 of gate body 34.

Pins 42 and 43 engage into a gate 44 which is slid over the cylindrical end section of housing 40.

Figure 5:
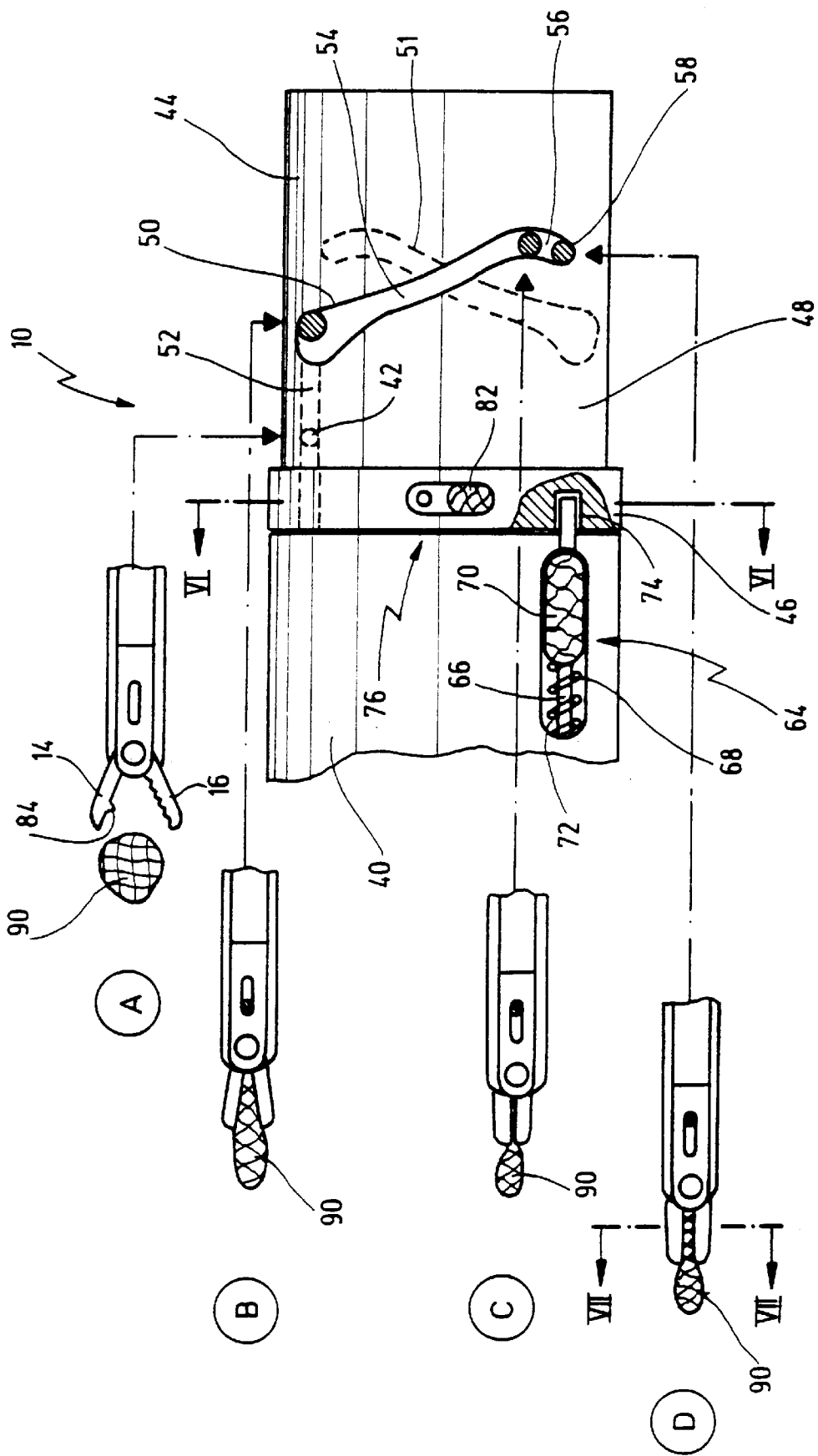
FIG. 5 shows a partial and partly cutaway side view of the grip of the device of FIG. 1, four positions A, B, C, and D of the mouth parts being indicated.

A side view of gate 44 is shown in FIG. 5.

Gate 44 has distally an annular flange 46 which sits on a shoulder on the exterior of housing 40. Proximally, gate 44 has a hollow-cylindrical section 48 which is slid onto the exterior of the cylindrical end section of housing 40.

Two grooves 50, 51 are cut in diametrically opposing fashion into hollow-cylindrical section 48 of gate. 44. Pins 42 and 43 of gate body 34 engage into grooves 50 and 51, respectively. Corresponding cutouts are present for this purpose in housing 40. Groove 50 (and, in correspondingly rotationally symmetrical fashion, groove 51) has an axial section 52 into which pin 42 of gate body 34 engages. Axial section 52 opens toward annular flange 46 of gate 44. This makes it possible firstly, after gate body 34 has been mounted on actuation element 22, to slide gate 44 from the proximal end onto said element; and it is additionally possible for the assembly made up of actuation element 22 and gate body 34 to move axially along axial section 53.

Adjoining the proximal end of axial section 52 of groove 50 is a circumferential section 54 which rises in the proximal direction. This rising section 54 ends in a circumferential end section 56 sloping downward in the distal direction, the closed end of which forms a stop 58.

The transition from axial section 52 into circumferential section 54 rising in the proximal direction is configured so as to accommodate adjustability via adjusting screw 28 and the resulting change in the relative displacement position between pusher sleeve 24 and actuation element 22, as well as differences in the resistance force exhibited by objects held by the mouth parts, which can result in great differences in the partial opening angles of the mouth parts upon application of the pre-holding force.

As shown in FIG. 5, a closure cap 60 is slid snugly over gate 44 in order to close off the grooves with a correspondingly ergonomic configuration, as is evident from FIGS. 1 through 4. Closure cap 60 thus sits in nonpositively fixed fashion on gate 44, and the assembly made up of closure cap 60 and gate 44 forms a rotatable section 62 of grip 18.

As is evident from FIGS. 1 through 3 and 5, a lock 64 is provided in housing 40.

Lock 64 has an axially extending stud 66 which is acted upon by the force of a spring 68 in such a way that it moves gate 44 in the proximal direction. Stud 66 is joined to a slide element 70 which is arranged in a recess 72 in housing 40. The contour of slide element 70 is such that it does not radially project beyond the housing, but nevertheless cap be grasped and actuated, i.e. displaced, from the outside with a finger. Lock 64 is arranged so that the tip of stud 66 is oriented toward the annular end surface of annular flange 46.

Figure 6:
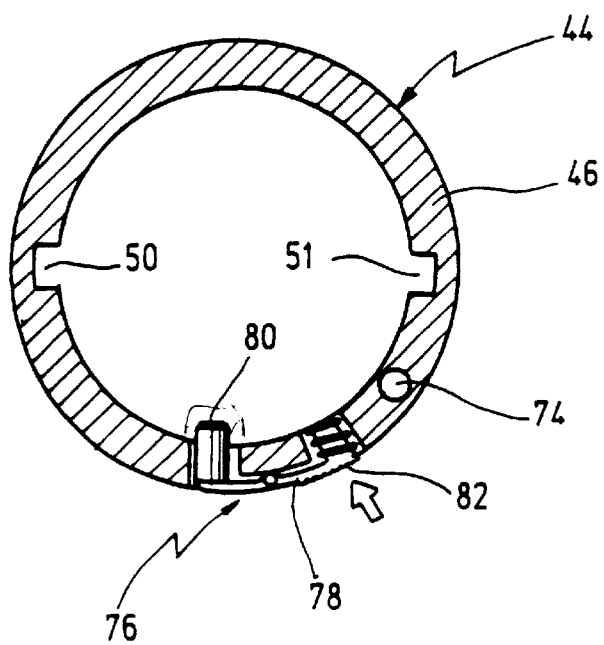
FIG. 6 shows a section along line VI—VI in FIG. 5.

As shown in the sectioned representation of FIG. 6, a blind hole 74 is provided in annular flange 46, into which stud 66 can travel. This occurs in the rotational position shown in FIG. 5, which corresponds to a final closed position D, as will be explained in more detail later.

In this locked position, as is evident from FIG. 5, no further relative rotation is possible between gate 44 and housing 40.

Also evident from FIGS. 5 and 6 is the fact that a circumferentially arranged interlock 76, which prevents gate 44 from sliding axially off housing 40, is arranged in the region of annular flange 46 of gate 44.

Interlock 76 has a rocker 78, one of whose ends is equipped with a locking peg 80. Locking peg 80 engages into a circumferential recess on the exterior of housing 40; it thus allows relative rotation between gate 44 and housing 40 about the shaft axis, but inhibits any axial sliding. The length of the circumferential opening is such that the final closed position is reached upon rotation of grip 18.

Rocker 78 has a pushbutton 82 on the side opposite locking peg 80. Pressure on pushbutton 82 causes locking peg 80 to snap out, so that gate 44 can be pulled off proximally from housing 40, for example for cleaning and sterilization purposes.

In the completely assembled state as shown in FIG. 4, there is placed between flange 94 of housing 40 and gate body 34 slid onto actuation element 22 a helical spring 92 which is pre-loaded so that the assembly made up of actuation element 22 and gate body 34 is pushed in the proximal direction. In the position shown in FIG. 4, mouth parts 14 and 16 are closed by the force of spring 92.

Forceps 10 is handled so that grip 18 is grasped with one hand, and one thumb is used to press onto pusher 26, as shown in FIG. 1 by an arrow 27. The rotatable part of grip 18 is in the position in which the device is "opened," i.e. pin 42 is located in axial section 52 of groove 50. Actuation element 22 is thereby displaced against the force of spring 92 toward the distal end, and mouth parts 14 and 16 are maximally spread, for example to an opening angle of approx. 50 degrees.

This pushing-in movement is limited by the fact that gate body 34 encounters a step 41, i.e. the stop, on the interior of housing 40. This open position is labeled A in FIG. 1 and FIG. 5. Pin 42 is displaced from the position of FIG. 4 along axial section 52 of groove 50, and has reached the position marked in FIG. 5 by the arrow proceeding from position A. In this position it is now possible to place an object, for example a spherical sponge 90 made of muslin material, between mouth parts 14 and 16. Provided on mouth part 14 is at least one tooth 84 which can engage into a corresponding gap 86 on the other mouth part 16, as is also evident from the sectioned representation of FIG. 7.

Once spherical sponge 90 has been introduced between mouth parts 14 and 16, pusher 26 is released and the preloaded spring 92 displaces the assembly made up of actuation element 22 and gate body 34 toward the proximal end, thus causing mouth parts 14 and 16 to close somewhat until they have reached the position labeled B in FIG. 5. In this partially closed position, spherical sponge 90 is caught between mouth parts 14 and 16 and is held with a pre-holding force due to the force of spring 92.

Pin 42 has now moved along axial section 52 of groove 50 into the position indicated in FIG. 5 by the arrow proceeding from position B. In this position, pin 42 is also located at the beginning of rising section 54 of groove 50. The transition region from axial section 52 into the circumferential and axially rising section 54 of groove 50 is configured so that a change in the relative displacement position between pusher sleeve 24 and actuation element 22, and a difference in the resistance presented by objects to be held in the mouth parts, which can result in different partial opening angles of the mouth parts upon application of the pre-holding force, can be accommodated.

The assembly made up of closure cap 60 and gate 44, forming rotatable section 62 of grip 18, is now rotated about the shaft axis, as shown by the transition from FIG. 2 to FIG. 3.

In the process, pin 42 moves first, along rising section 54 of groove 50 and then into the downward-sloping end section 56 until stop 58 is reached.

In FIG. 5, the letter C designates the intermediate position in which pin 42 has just reached the transition from rising section 54 to the downward-sloping end section 56. In this state, actuation element 22 together with gate body 34 is moved maximally in the proximal direction against the resistance offered by the object held by the mouth parts. This assembly then moves slightly back again toward the distal end until it then reaches the final closed position D.

The coacting parts—gate 44, gate body 34, and actuation element 22 joined to the latter—form an device 30 which operates as a rigid linkage to move mouth parts 14 and 16 positively into the defined final closed position D.

In this final closed position D, as evident from both FIG. 5 and FIG. 6, spherical sponge 90 is held with a predetermined force between mouth parts 14 and 16.

Figure 7:
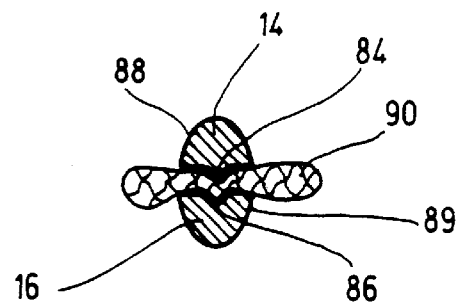
FIG. 7 shows a section along line VII—VII in FIG. 5.

It is evident from the sectioned representation of FIG. 7 that mouth parts 14 and 16 each have the cross-sectional profile of a semi-oval 88, 89. The overall result, for the closed mouth parts in the final closed position D, is an approximately oval outer contour which allows dissection with the closed mouth parts 14 and 16.

In the final closed position D, gate 44 is rotated so that its blind hole 74 comes to rest in front of stud 66 of lock 64, so that spring 68 now slides stud 66 into the blind hole and closes lock 64. Forceps 10 can now be introduced into a body, for example through a trocar, and corresponding dissection operations can be performed.

After withdrawal from the trocar, stud 66 is displaced by way of slide element 70 against the force of spring 68, and lock 64 is released. Rotatable section 60 is then rotated in a direction opposite to the one described previously, so that mouth parts 14 and 16 are partially opened again, i.e. have once again reached the position shown in FIG. 2. Pressure is then exerted again on pusher 26 in order to spread mouth parts 14 and 16 to their maximum extent, so that spherical sponge 90 can be removed and, for example, replaced by another one.

Figure 8:
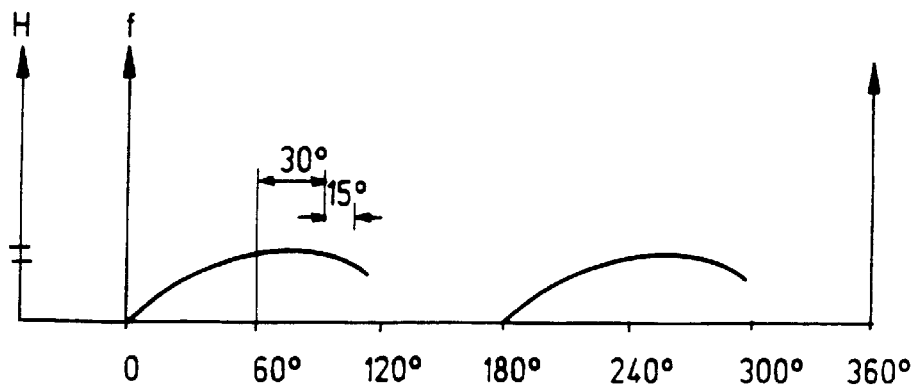
FIG. 8 shows a force/displacement diagram as a function of the rotation angle of the rotatable grip element.

FIG. 8 depicts a diagram which shows the force f and linear stroke H of actuation element 22 as a function of the rotation angle of rotatable section 62 of grip 18. The very small displacements of actuation element 22 result in a relatively flat curve with a corresponding torque, i.e. the rotary movement that occurs is acted upon by a relatively uniform force, and is inhibited once the stop is reached. The displacement of slide element 70 of lock 64 indicates to the operator that rotatable section 62 has been rotated into the correct position, and that mouth parts 14 and 16 are now being acted upon by the desired holding force. Application of additional force onto rotatable section 62 causes no further movement of mouth parts 14 and 16. The applied forces are then diverted onto grip 18. The position corresponds to a "closed" or "ON" position. These positions can be indicated on the grip, for example, by the words "ON" and "OFF".

In FIG. 4, reference numbers 95 and 96 designate flushing orifices in flange 94 and in conical section 36 of the gate body, so that the entire interior can be flushed for cleaning purposes. A laterally protruding fitting 98, through which a flushing or cleaning liquid can be delivered and passed through the grip via cleaning openings 95 and 96, is provided for this purpose on shaft 12.

Figure 9:
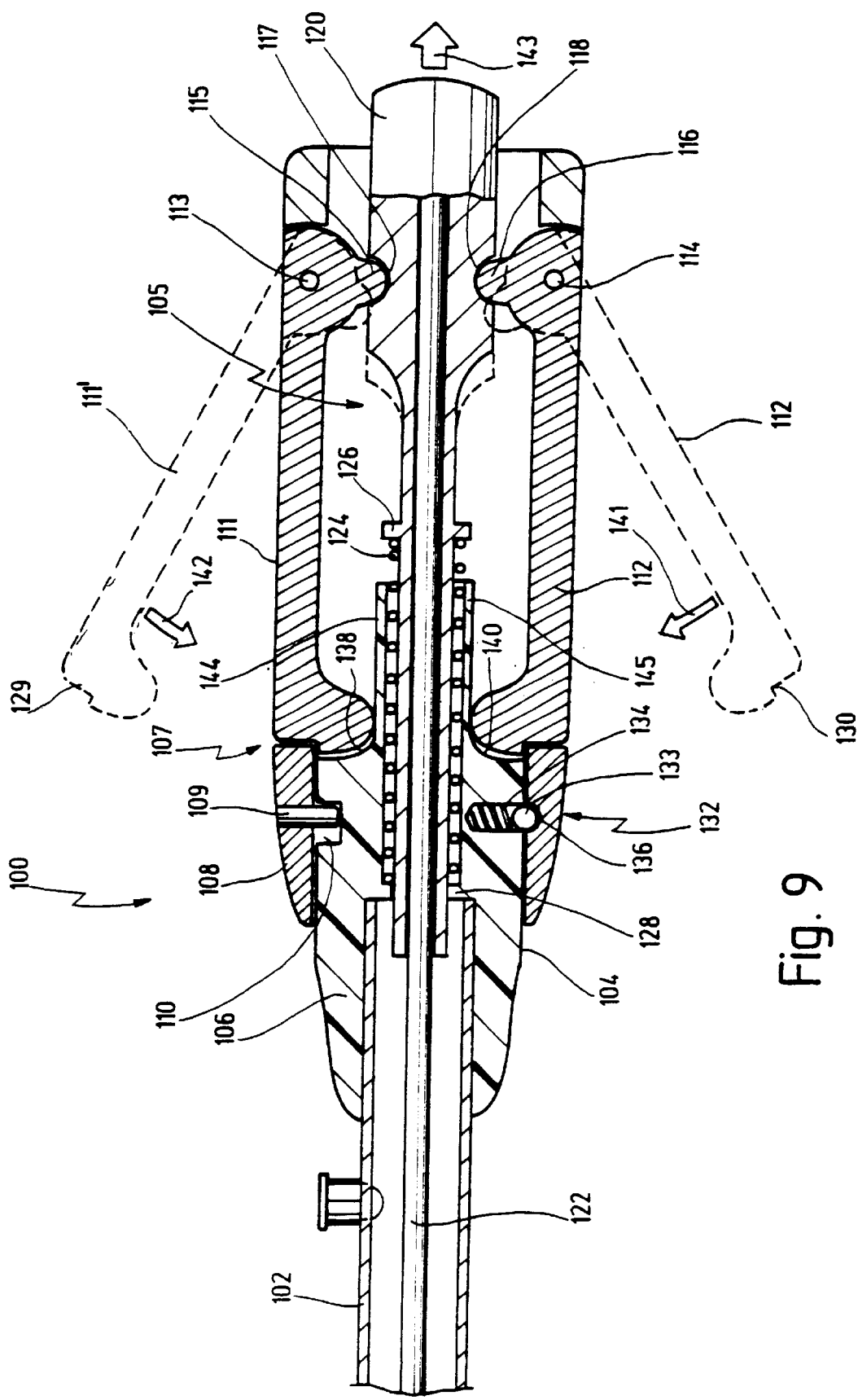
FIG. 9 shows a section view, comparable to the section view of FIG. 4, of a second exemplifying embodiment having levers which can swing out laterally.

The further exemplifying embodiment shown in FIG. 9 shows a forceps 100 only in the region of its grip 104.

Forceps 100 also has at its distal end two mouth parts which are mounted on a shaft 102.

An actuation element 122 extending through shaft 102 is equipped, as described above, with a pusher sleeve 120 at the end.

A spring 124 extends between an internally projecting flange 128 of a housing 106 and a corresponding outer annular flange 126 on pusher sleeve 120.

In housing 106, which is joined immovably to shaft 102, two levers 111, 112 are arranged, diametrically opposite one another, in two longitudinal grooves 138 and 140 cut out of housing 106. Levers 111 and 112 are pivotable about axes 113 and 114, respectively. Two short lever arms of each lever 111, 112 beyond axes 113, 114 are configured respectively as knobs 115 and 116, which engage into corresponding recesses 117 and 118 on the exterior of pusher sleeve 120.

In the sectioned representation of FIG. 9, the two levers 111, 112 are shown with solid lines in their swung-in or flush position; this position corresponds to the final closed position D of the mouth parts as described above. In order to lock levers 111, 112 in this position, there is provided on each of them a step 129, 130 onto which a lock 107 in the form of a slide bushing 108 can be slid, as shown in the sectioned view of FIG. 9. Slide bushing 108 is equipped with a radially inwardly projecting peg 109 which is received in a corresponding opening 110 on the exterior of housing 106. Opening 110 limits the axial displacement travel of slide bushing 108.

In the locking displacement position shown in the sectioned view of FIG. 9, slide bushing 108 is additionally secured by a ball catch 132. A spring 134 which rests radially outwardly on a ball 133 is received in a blind hole located approximately diametrically opposite peg 109. Spring 134 pushes ball 133 into a corresponding recess 136 on the interior of slide bushing 108.

When slide bushing 108 is displaced distally, overcoming the inhibiting force of ball catch 132, slide bushing 108 moves out of steps 129, 130 of levers 111, 112, and the latter can be swung outward about their corresponding axes 113, 114.

A position of this kind is indicated in FIG. 9 by the dashed lines. In this position, knobs 115, 116 have also displaced pusher sleeve 120 in the distal direction, thereby opening the mouth parts. By further pressure on pusher sleeve 120 the mouth parts can, if applicable, be opened even further, thus also spreading levers 111, 112 farther apart.

The assembly made up of levers 111, 112 and pusher sleeve 120 thus forms device 105, operating as a rigid linkage, for moving the mouth parts in positive and defined fashion into the final closed position D described above.

This is done by swinging levers 111, 112 inward from the position shown with dashed lines in FIG. 9, as shown by arrows 141 and 142, respectively. The assembly made up of pusher sleeve 120 and actuation element 122 thereby moves in the proximal direction, as shown by an arrow 143.

This displacement distance corresponds to the second portion, described above, of the action of device 105. Once levers 111, 112 are completely flush against housing 106, slide bushing 108 is slid over their steps 129 and 130 to prevent them from swinging outward.

A base 144, 145 of each longitudinal groove 138, 140 constitutes a stop beyond which levers 111, 112 cannot be displaced farther inward.

The embodiment shown in FIG. 9 is also correspondingly provided with flushing orifices (not shown here), so that here again the interior can be flushed with a cleaning liquid through a lateral fitting (not designated in detail here).

What is claimed is:

1. A surgical grasping and holding forceps comprising:
    shaft with at least two mouth parts which are arranged at a distal end of said shaft;
    a grip which is arranged at a proximal end of said shaft;
    a mechanism, in working engagement with said grip and with said mouth parts, for opening and closing said mouth parts, said mechanism having a spring exerting a spring force, said mechanism being acted upon by said spring force in such a way that said mouth parts are thereby pushed in a closing direction, and said mechanism is movable against said spring force by manipulation at said grip, in such a way that said mouth parts open;
    a lock for locking said mouth parts in a definite position;
    a device, configured as a rigid linkage and engaging into said mechanism, with which device said mouth parts are positively movable into a defined final closed position in which they exert a predefined holding force on an object received between said mouth parts, said device having a stop which prevents overshooting of said final closed position, even when a greater force is applied, and wherein said lock locks said mouth parts in that final closed position; and
    wherein said device has at least one lever, articulated on said grip, whose one end is in engagement with said mechanism for opening and closing, and whose other end is swung out laterally when said mouth parts are in an open position, the other end being swingable onto said grip in order to move said mouth arts into said final closed position.

2. The surgical grasping and holding forceps of claim 1, wherein in said final closed position the at least one lever extends along said elongated grip.

3. The surgical grasping and holding forceps of claim 2, wherein there is cut out from said grip a longitudinal groove into which said lever can be snugly received when said mouth parts are in said final closed position, so that it does not project beyond a contour of said grip.

4. The surgical grasping and holding forceps of claims 3, wherein two levers, arranged diametrically opposite one another, are provided.

5. The surgical grasping and holding forceps of claim 4 wherein said lock is configured as a slide bushing, which when said lever is swung onto said grip, can be slid over it and keeps it from swinging outward.

6. The surgical grasping and holding forceps of claim 5, wherein said slide bushing is locked by way of a ball catch when said mouth parts are in said final closed position.

7. The surgical grasping and holding forceps of claim 6, wherein said mechanism for opening and closing said mouth parts has an actuation element, axially displaceable in said shaft, which actuation element is connected to one end of said lever in such a way that a pivoting movement of said lever end can be converted into an axial displacement movement of said actuation element.

* * * * *